(12) United States Patent
Lawson et al.

(10) Patent No.: US 8,262,663 B2
(45) Date of Patent: Sep. 11, 2012

(54) ENDPLATE PREPARATION INSTRUMENT

(75) Inventors: Jonathan Lawson, Cambridge (GB);
Scott Johnson, Newmarket (GB);
Robert Snell, Ashley (GB); Geoffrey Thomas Andrews, Cambridge (GB)

(73) Assignee: Ranier Limited, Cambridge (GB)

( * ) Notice: Subject to any disclaimer, the term of this patent is extended or adjusted under 35 U.S.C. 154(b) by 1070 days.

(21) Appl. No.: 12/115,054

(22) Filed: May 5, 2008

(65) Prior Publication Data
US 2009/0275943 A1 Nov. 5, 2009

(51) Int. Cl.
*A61F 2/46* (2006.01)
(52) U.S. Cl. ........................................ 606/86 R
(58) Field of Classification Search ............ 606/79, 606/85, 86 R, 86 A
See application file for complete search history.

(56) References Cited

U.S. PATENT DOCUMENTS

| | | | |
|---|---|---|---|
| 5,342,365 A | 8/1994 | Waldman | |
| 6,896,680 B2 | 5/2005 | Michelson | |
| 6,966,912 B2 | 11/2005 | Michelson | |
| 7,160,304 B2 | 1/2007 | Michelson | |
| 2003/0135277 A1* | 7/2003 | Bryan et al. | 623/17.12 |
| 2004/0002712 A1 | 1/2004 | Grinberg et al. | |
| 2004/0215197 A1 | 10/2004 | Smith et al. | |
| 2005/0065529 A1 | 3/2005 | Liu et al. | |
| 2005/0113842 A1 | 5/2005 | Bertagnoli et al. | |
| 2006/0089649 A1 | 4/2006 | Ullrich, Jr. et al. | |
| 2006/0129160 A1 | 6/2006 | Liu et al. | |
| 2006/0167461 A1 | 7/2006 | Hawkins et al. | |
| 2006/0206117 A1 | 9/2006 | Harp | |
| 2007/0162041 A1 | 7/2007 | Robie et al. | |
| 2007/0233131 A1 | 10/2007 | Song et al. | |
| 2007/0270863 A1 | 11/2007 | Melkent | |

FOREIGN PATENT DOCUMENTS

WO    WO 2004/002332 A1    1/2004

OTHER PUBLICATIONS

Harmony Port System, Abbott Spine http://international.abbottspine.com/index.php?id=62 (printed May 12, 2008).

* cited by examiner

*Primary Examiner* — Nicholas Woodall
(74) *Attorney, Agent, or Firm* — Wolf, Greenfield & Sacks, P.C.

(57) ABSTRACT

An instrument for preparation of vertebral endplates and a method of preparing a surface of a vertebral endplate are described. The instrument includes a body having a frame, an endplate preparation member supported by the body, and a pivot point. A tilt axis is perpendicular to and intersects a sweep axis at the pivot point. The endplate preparation member is coupled to the frame and controllably pivotable in an arc about the first tilt axis to change a tilt of the endplate preparation member. The endplate preparation member is also controllably pivotable in an arc about the sweep axis while maintaining the tilt of the endplate preparation member. By sweeping the endplate preparation member at incrementally larger tilt angles, recesses in a vertebral endplate surface are gradually formed, which may allow greater precision and control of a depth of the recesses and reduce stress on the vertebral endplate, as opposed to more aggressive techniques.

23 Claims, 9 Drawing Sheets

```
┌─────────────────────────────────────────────────┐
│ Provide a vertebral endplate preparation instrument, 410. │
└─────────────────────────────────────────────────┘
                         ↓
┌─────────────────────────────────────────────────┐
│ Insert a distal portion of the instrument into a disc space │
│ adjacent to a vertebral endplate, 420.          │
└─────────────────────────────────────────────────┘
                         ↓
┌─────────────────────────────────────────────────┐
│ Pivot the first preparation member relative to a vertebral │
│ endplate about a first tilt axis, 430.          │
└─────────────────────────────────────────────────┘
                         ↓
┌─────────────────────────────────────────────────┐
│ Set the instrument to controllably maintain a desired tilt angle, │
│ 435.                                            │
└─────────────────────────────────────────────────┘
                         ↓
┌─────────────────────────────────────────────────┐
│ Pivot the first preparation member relative to the vertebral │
│ endplate about a first sweep axis while the first endplate │
│ preparation member is in contact with a surface of the │
│ vertebral endplate, 440.                        │
└─────────────────────────────────────────────────┘
                         ↓
┌─────────────────────────────────────────────────┐
│ Pivot the first preparation member about the first tilt axis until │
│ a second desired tilt angle is reached, 450.    │
└─────────────────────────────────────────────────┘
                         ↓
┌─────────────────────────────────────────────────┐
│ Pivot the first preparation member about the first sweep axis │
│ while the second desired tilt angle is maintained, 460. │
└─────────────────────────────────────────────────┘
                         ↓
┌─────────────────────────────────────────────────┐
│ Pivot the first preparation member relative to the frame about │
│ the first tilt axis until the instrument is in a collapsed │
│ configuration, 470.                             │
└─────────────────────────────────────────────────┘
                         ↓
┌─────────────────────────────────────────────────┐
│ Withdraw the distal portion of the instrument from the disc │
│ space while maintaining the instrument in a collapsed │
│ configuration, 480.                             │
└─────────────────────────────────────────────────┘
```

*FIG. 8*

ENDPLATE PREPARATION INSTRUMENT

RELATED APPLICATIONS

This application is related to co-pending U.S. patent application Ser. No. 12/115,043 entitled "DISTRACTOR," filed on May 5, 2008, which is herein incorporated by reference in its entirety.

FIELD OF INVENTION

The present invention relates to an instrument for preparing an endplate of a vertebra.

BACKGROUND

A spinal disc lies between endplates of adjacent vertebrae. The disc stabilizes the spine and assists in distributing forces between vertebral bodies. A spinal disc may be displaced or damaged due to trauma, disease or other degenerative processes that can occur over time. For example, a portion of the disk may weaken or tear which can result in the protrusion of the nucleus pulposus into a region of the spine (e.g., the vertebratal foramen) that includes spinal nerves. The protruding nucleus pulposus may press against spinal nerves causing pain, numbness, tingling, diminished strength and/or a loss of motion. Another common degenerative process is the loss of fluid from the disc. Such fluid loss can limit the ability of the disc to absorb stress and may reduce its height, which can lead to further instability of the spine, as well as decreasing mobility and causing pain.

To address the conditions described above, a displaced or damaged spinal disc may be surgically removed from the spine. Historically, after the disc is removed, a fusing implant is inserted into the disc space that allows the two adjacent vertebrae to fuse together. In other surgical procedures, the damaged disc is removed and replaced with an artificial disc. Specialized instruments have been provided to facilitate preparation of the site, which will receive the artificial disc.

SUMMARY

An aspect of the invention relates to a surgical instrument for preparing a surface of a vertebra. The instrument includes an elongated body having a frame, a first pivot point and a first endplate preparation member for preparing a surface of a vertebra. A first sweep axis and a first tilt axis that is substantially perpendicular to the first sweep axis pass through the first pivot point. The first endplate preparation member is supported by the body and controllably pivotable in an arc about the first tilt axis to change a tilt of the first endplate preparation member, and is controllably pivotable in an arc about the first sweep axis while maintaining a tilt of the first endplate preparation member.

Another aspect of the invention relates to a surgical instrument for preparing a surface of a vertebra having an elongated body with a frame, a first pivot point though which a first sweep axis passes, and a first endplate preparation member that is controllably pivotable in an arc about the first sweep axis. The first endplate preparation member is supported by the body and is controllably pivotable through a predetermined sweep range of greater than about 3 degrees and less that about 180 degrees. The first endplate preparation member is also able to be displaced along the first sweep axis changing a height of the first endplate preparation member.

Yet another aspect of the invention relates to a surgical instrument for preparing a surface of a vertebra including an elongated body having a frame and a first arm configured to cooperate with a first endplate preparation member. The first arm is controllably pivotable with respect to the frame about a first arm-sweep axis for controllably pivoting the first endplate preparation member about a first sweep axis that is substantially parallel to the first arm-sweep axis. The instrument is configured to controllably pivot the first endplate preparation member about a first tilt axis that is substantially parallel to and intersects the first sweep axis.

Another aspect of the invention relates to a preparation member unit for preparing a surface of a vertebra, The preparation member unit includes a first endplate preparation member having a portion configured to couple with an actuator of an instrument body and a mounting member configured to mount the preparation member unit to a frame portion of an instrument body. The preparation member unit also includes a first preparation member-mounting coupling that pivotably couples the endplate preparation member and the mounting member allowing the first endplate preparation member to pivot relative to the mounting member about a first sweep axis and about a first tilt axis that is perpendicular to, and intersects, the first sweep axis at a first pivot point.

Yet another aspect of the invention relates to an instrument body having a frame portion and an actuator coupled with the frame portion. The frame portion is configured to couple with a mounting member of a preparation member unit. The actuator is configured to cooperate with a first endplate preparation member of the preparation member unit. The actuator is also configured to controllably pivot the first endplate preparation member about a first sweep axis, and configured to pivot the first endplate preparation member about a first tilt axis that is substantially perpendicular to, and intersects, the first sweep axis.

Another aspect of the invention relates to an endplate preparation member for preparing a surface of a vertebra. The endplate preparation member includes a body portion with a first preparation surface, at least one endplate preparation element extending from the first preparation surface, and an extension of the body portion configured for engagement with a coupling in an instrument body. The body location also includes a pivot location being configured for movement about a tilt axis and about a sweep axis that is substantially perpendicular to the tilt axis and that passes through the pivot location.

Yet another aspect of the invention relates to a method of preparing a surface of a vertebral endplate. The method includes providing a vertebral endplate preparation instrument having a first endplate preparation member located at a distal portion of the instrument and inserting the distal portion of the instrument into a disc space adjacent to the vertebral endplate. The method also includes pivoting the first endplate preparation member relative to the vertebral endplate about a first tilt axis. The method further includes pivoting the first endplate preparation member relative to the vertebral endplate about a first sweep axis that is substantially perpendicular to the first tilt axis while the first endplate preparation member is in contact with the first vertebral endplate surface.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

A vertebral endplate may be prepared to receive an implantable spinal disc and such preparation may include the formation of an endplate surface that is compatible with the contours and/or surface of the replacement disc. For example, the spinal disc may include certain projections intended for placement in complementary recesses to be formed in the vertebral endplate, and the instrument and methodology of the invention may be employed to achieve the same. An exemplary embodiment includes an instrument with a body having an elongated frame, a first pivot point, and a first endplate preparation member for preparing a surface of a vertebra. A first sweep axis and a first tilt axis that is substantially perpendicular to the first sweep axis intersect at the first pivot point. The first endplate preparation member is supported by the body and is controllably pivotable with respect to the frame about the first tilt axis to change a tilt of the first endplate preparation member, and controllably pivotable about the first sweep axis while maintaining the tilt. Teeth or other endplate preparation effectors may be incorporated in the first endplate preparation member, such that a sweeping motion of the first endplate preparation member will form recesses in the vertebral endplate.

The angular extent, or length, of a recess formed in a vertebral endplate may be controlled by limiting a total range of angular sweep of the first preparation member. For example, an inner frame width may limit the total range of angular sweep of the first preparation member. By allowing a user to controllably select a tilt angle of the first endplate preparation member with respect to the frame, depths of recesses formed in the vertebral endplate may be controlled.

A user may gradually form recesses in the vertebral endplate by initially "sweeping" the first endplate preparation member against the vertebral endplate at a small tilt angle, then "sweeping" against the vertebral endplate at incrementally larger tilt angles. Gradually forming recesses may allow greater control of the first endplate preparation member as the recesses are formed, which may result in greater control of a final depth of the recesses. Gradually forming recesses may also reduce a risk of damage to vertebrae during endplate preparation, as compared to more aggressive endplate preparation techniques. In addition, a user may receive tactile feedback regarding force applied to the vertebral endplate by the first preparation member during execution of a sweep through a first arm of the instrument.

Reducing a tilt angle of the first endplate preparation member may reduce the profile of the instrument, facilitating insertion and/or withdrawal of the working end of the instrument from the disc space. The instrument may include a tilt lock to maintain a selected tilt of the first endplate preparation member. The instrument may include a reduction actuator configured to place the first endplate preparation member in a reduced tilt configuration.

In some embodiments, an instrument with a first endplate preparation member and a second endplate preparation member is provided. The second endplate preparation member may be controllably pivotable about a second sweep axis that is substantially Is parallel to a first sweep axis, and controllably pivotable about a second tilt axis that is substantially perpendicular to the second sweep axis. Movement of the second endplate preparation member may be mechanically coupled to movement of the first endplate preparation member, or the second endplate preparation member and the first endplate preparation member may move independently.

Some embodiments of the invention provide an endplate preparation unit. Other embodiments of the invention provide an instrument body. The endplate preparation unit and the instrument body are configured to couple to each other, forming an endplate preparation instrument with the endplate preparation member at the tip of the device. A frame of the endplate preparation instrument may include a distal frame portion of the endplate preparation unit that mounts to a frame portion of the instrument body. The endplate preparation unit may include a distal frame portion, one or more endplate preparation members that are pivotably coupled to the distal frame portion so as to be moved in a sweeping and a tilting direction relative to respective sweeping and tilting axes of the distal frame portion, and where the distal frame portion is configured for connection to the frame portion of the instrument body.

The instrument body may include a frame portion configured to couple with the distal frame portion of the preparation member unit, and an actuator system for manipulating the sweep and tilt of the endplate preparation member. The actuator may be configured to controllably exert a force to pivot the endplate preparation member about a first sweep axis, and to controllably exert a force to pivot the endplate preparation member about a first tilt axis that is substantially perpendicular to the first sweep axis.

Another embodiment of the invention is an endplate preparation member that may be used with a preparation member unit and/or with an endplate preparation instrument. The endplate preparation member includes a first preparation surface and one or more primary cutting projections extending from the first preparation surface. The primary cutting projections are configured to form primary fixation recesses for receiving primary fixation elements of the implant. The endplate preparation member may also include dome-cutting projections configured to form a recess with a substantially domed shape for receiving an implant, such as an artificial disc. A configuration of the endplate preparation member may permit forming the overall dome shaped implant receiving recess and the primary fixation recesses simultaneously.

Other embodiments provide a method of endplate preparation using a vertebral endplate preparation instrument. Initially, an instrument is provided with a first endplate preparation member. A distal portion of the instrument is inserted into a disc space adjacent to a vertebral endplate. The instrument may be in a collapsed configuration as the distal portion is inserted into the disc space. The first endplate preparation member is pivoted relative to vertebral endplate about a first tilt axis until a first desired tilt angle is reached. The instrument may be set to controllably maintain the first desired tilt angle. Then, the first endplate preparation member is pivoted relative to the vertebral endplate about a first sweep axis, while the first endplate preparation member is in contact with a surface of the first vertebral endplate. After the disc is prepared, the distal portion of the instrument may be withdrawn from the disc space, while the instrument is in a reduced tilt collapsed configuration. The tilt of the endplate preparation member may be adjusted to increase the depth of the recesses formed in the bone surface.

Figure 1A:
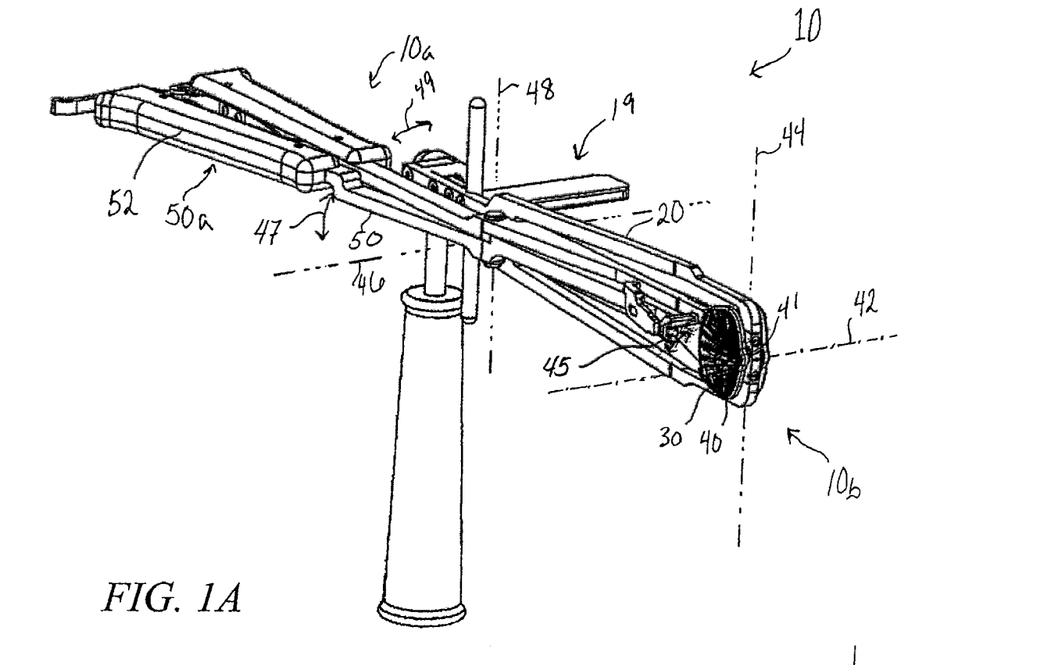
FIG. 1A is front perspective of an endplate preparation instrument, in accordance with an illustrative embodiment of the present invention.
Figure 1B:
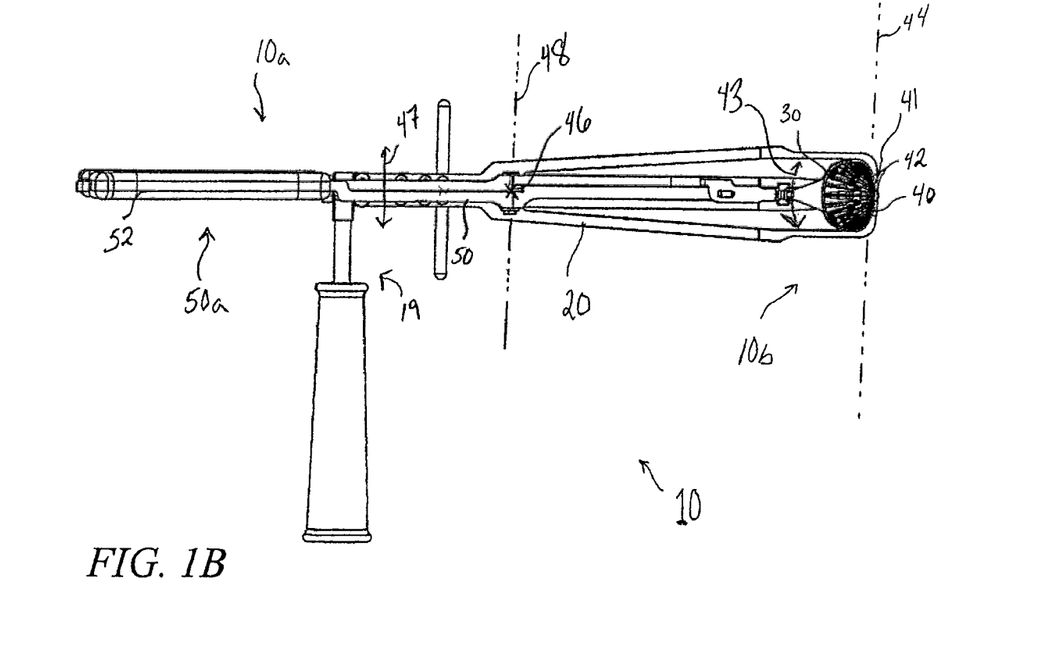
FIG. 1B is a side view of the instrument depicted in FIG. 1A.

Turning to FIGS. 1A and 1B, an exemplary endplate preparation instrument 10 including a body 19 with an elongated frame 20, a first pivot point 40, and a first endplate preparation member 30 for preparing a surface of a vertebra, is illustrated. The first endplate preparation member 30 is supported by the body 19. As depicted, the first endplate preparation member 30 is pivotably coupled to the frame 20. During preparation of a vertebral endplate, after a distal portion 10b of the instrument in inserted into a disc space, the frame 20 may maintain a fixed position relative to a vertebra while the first endplate preparation member 30 moves with respect to the frame 20 and the vertebra.

The first pivot point 40 may be located at the distal portion 10b of the instrument. As shown in the perspective view of FIG. 1A, a first sweep axis 42, and a first tilt axis 44 that is substantially perpendicular to the first sweep axis 42, both pass through the first pivot point 40. The first endplate preparation member 30 is controllably pivotable in an arc 45 about the first tilt axis 44 to change a tilt of the first endplate preparation member 30, and controllably pivotable in an arc 43 about the first sweep axis 44 while maintaining the tilt of the first endplate preparation member 30. The first endplate preparation member 30 may be controllably pivotable about the first tilt axis 44 and controllably pivot about the first sweep axis 42 simultaneously.

In some embodiments, this is accomplished through a first preparation member-frame coupling 41 that couples the first endplate preparation member 30 and the frame 20, and that is configured to allow the first endplate preparation member 30 to controllably pivot relative to the frame 20 in an arc 45 about the first tilt axis 44 to change a tilt of the first endplate preparation member 30. In some embodiments, the first preparation member-frame coupling 41 is releasable and in other embodiments the first preparation member-frame coupling may not be releasable. As used herein, changing the "tilt" of the first endplate preparation member 30 includes, but is not limited to, pivoting the first endplate preparation member 30 about the first tilt axis 44. As shown in the side view of FIG. 1B, the first preparation member-frame coupling 41 may also be configured to allow the first endplate preparation member 30 to controllably pivot relative to the frame 20 in an arc 43 about the first sweep axis 42 to change a "sweep position" of the first endplate preparation member 30 while maintaining the "tilt" of the first endplate preparation member 30. As used herein, changing the "sweep position" of the first endplate preparation member 30 includes, but is not limited to, pivoting the first endplate preparation member 30 about the first sweep axis 42.

In some embodiments, the instrument 10 may include a first arm 50 configured to cooperate with the first endplate preparation member 30. The first arm 50 may be pivotably coupled with the frame 20 allowing the first arm 50 to controllably pivot with respect to the frame 20 in an arc 47 about a first arm-sweep axis 46, which is substantially parallel to the first sweep axis 42. Due to coupling between the first arm 50 and the first endplate preparation member 30, moving a proximal first arm portion 50a along arc 47 with respect to the frame 20 changes a sweep position of the first endplate preparation member 30. The proximal first arm portion 50a may include a first grip 52 allowing a user to more easily grasp and control a position of the proximal first arm portion 50a. The first arm 50 may form a portion of an actuator for controllably pivoting the first preparation member 30 about the first sweep axis 42, In some embodiments, the instrument is configured to controllably pivot the first endplate preparation member about the first tilt axis 42. As depicted, the first arm 50 is pivotably coupled with the frame 20 of the instrument 10 allowing the first arm 50 to controllably pivot with respect to the frame 20 in an arc 49 about the first arm-tilt axis 48, which is parallel to the first tilt axis 44. Due to this coupling between the first arm 50 and the first endplate preparation member 30, moving a proximal first arm portion 50a along arc 49 with respect to the frame 20 changes a tilt angle of the first endplate preparation member 30. The first arm 50 may form a portion of an actuator for controllably pivoting the first preparation member 30 about the first sweep axis 42 and about the first tilt axis 44.

Figure 1C:
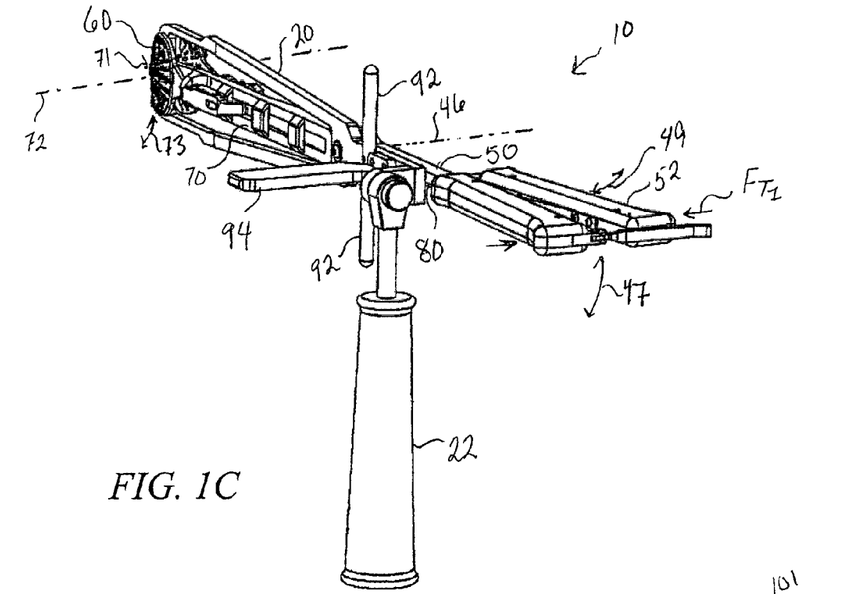
FIG. 1C is a back perspective view of the instrument depicted in FIG. 1A.
Figure 1D:
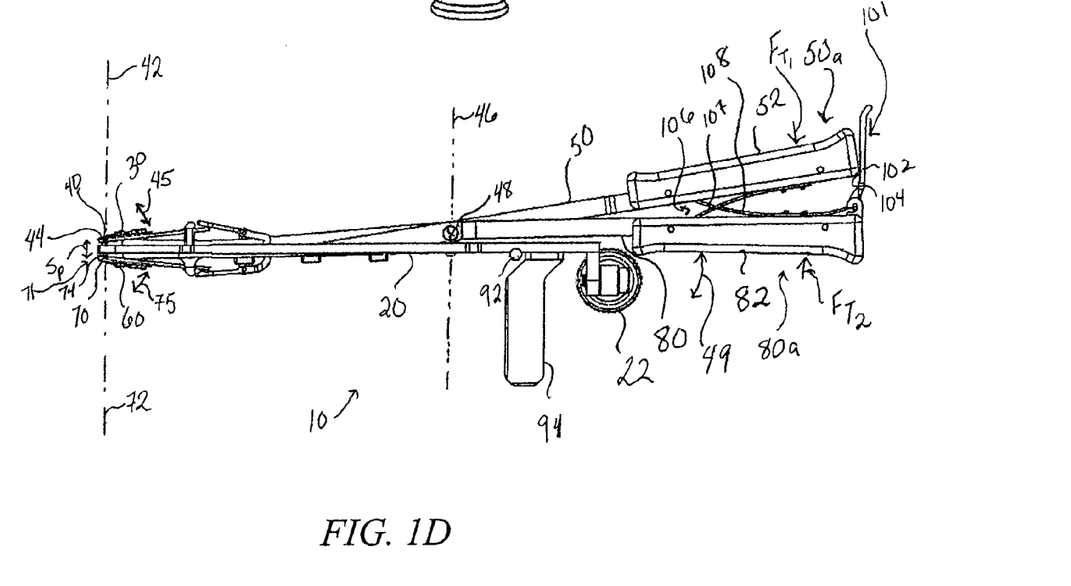
FIG. 1D is a top view of the instrument depicted in FIG. 1A.

Some embodiments of the endplate preparation instrument 10 may include a second pivot point 70 and a second endplate preparation member 60 for preparing a surface of a vertebra, as shown in FIGS. 1C and 1D. A second sweep axis 72 is substantially perpendicular to and intersects a second tilt axis 74 at the second pivot point 70. The second endplate preparation member 60 is coupled with the frame 20 in a configuration that allows the second endplate preparation member 60 to controllably pivot with respect to the frame 20 along an arc 73 about a second sweep axis 72. In the depicted embodiment, the second sweep axis 72 overlays the first sweep axis 42; however, in other embodiments the second sweep axis 72 is substantially parallel to, but spatially displaced from, the first sweep axis 42.

The second endplate preparation member 60 is controllably pivotable with respect to the frame 20 along an arc 75 about a second tilt axis 74 that is substantially parallel to the first tilt axis 44. As depicted, a second preparation member-frame coupling 71 couples the second endplate preparation member 60 and the frame 20, allowing the second endplate preparation member 60 to controllably pivot about the second sweep axis 72 and controllably pivot about the second tilt axis 74. In the depicted embodiment, the second tilt axis 74 is spatially displaced from the first tilt axis 44; however, in other embodiments the second tilt axis 74 may overlay the first tilt axis 44.

Some embodiments of an endplate preparation instrument 10 may include a second arm 80 configured to cooperate with the second endplate preparation member 60, as depicted. The second arm 80 may be pivotably coupled with the frame 20 allowing the second arm 80 to controllably pivot with respect to the frame 20 in an arc 47 about the first arm-sweep axis 46, which is substantially parallel to the first sweep axis 42 and the second sweep axis 72. Due to coupling between the second arm 80 and the second endplate preparation member 60, moving a proximal second arm portion 80a along arc 47 with respect to the frame 20 changes a sweep position of the second endplate preparation member 60. The proximal second arm portion 80a may include a second grip 82 allowing a user to more easily grasp and hold the proximal second arm portion 80a. The second arm 80 may form a portion of an actuator for controllably pivoting the second preparation member 60 with respect to the frame 20 about the second sweep axis 72.

In the depicted embodiment, the first arm 50 and the second arm 80 pivot together about the arm-sweep axis 46; however, in other embodiments the first arm 50 and the second arm 80 pivot in opposite directions along arc 47. In still other embodiments, the first arm 50 and the second arm 80 pivot with respect to the arm-sweep axis 46 independently of each other, as the invention is not limited in this respect.

In some embodiments, the first arm 50 and the second arm 80 diverge from each other as they extend from the first arm sweep axis at the frame 20 toward the distal portion of the instrument 10b. In some embodiments, the first arm 50 and the second arm 80 each bend so that the arms diverge laterally toward opposite sides of the frame 20 at the distal portion 10b of the instrument.

A coupling between the second arm 80 and the frame 20 may be configured to allow the second arm 80 to pivot with respect to the frame 20 about an arm-tilt axis 48 along arc 49. Due to coupling between the second arm 80 and the second endplate preparation member 60, moving a proximal second arm portion 80a along arc 49 with respect to the frame 20 changes a tilt of the second endplate preparation member 60.

Some embodiments of the invention permit control of a tilt of the first endplate preparation member 30 about the first tilt axis 44, and permit control of a tilt of the second endplate preparation member 60 about the second tilt axis 74. In the depicted embodiment, both the first arm 50 and the second arm 80 are may be used to control a tilt of the first endplate preparation member 30 and the second endplate preparation member. When the proximal first arm portion 50a and the proximal second arm portion 80a are pivoted closer to each other along arc 49, a tilt of the first proximal head 30 is increased and a tilt of the second proximal head 60 is increased. At the same time, spacing $S_p$ between the first pivot point 40 and the second pivot point 70 may increase, as is discussed below with respect to FIGS. 5A and 5B.

As depicted, moving the proximal first arm portion 50a and the proximal second arm portion 80a toward each other symmetrically with respect to the frame 20 results in the first endplate preparation member 30 and the second endplate preparation member 60 tilting symmetrically with respect to the frame 20. However, because the first arm 50 and the second arm 80 are both able to pivot with respect to the frame about tilt axis 48, the first arm 50 and the second arm 80 can each pivot by a different angle with respect to the frame 20 resulting in a different tilt angle for the first endplate preparation member 30 than for the second endplate preparation member 60. This "nonsymmetrical tilt" may allow the first endplate preparation member 30 and the second endplate preparation member 60 to conform or adjust to a disc space orientation that is not symmetrical with respect to the instrument frame 20.

Embodiments may include a tilt select component for selecting a preparation member tilt from a predefined set of tilt values and may include a tilt lock component for maintaining a selected tilt. In the depicted embodiment, a ratchet component 102 on a proximal portion 80a of the second arm and a complementary tooth component 104 on the proximal portion 50a of the first arm provide a predefined set of tilt values based on a spacing of projections on the ratchet component 102 forming a tilt selection component 101. The tilt selection component 101 allows an angle between the proximal portion 50a of the first arm and the proximal portion of the second arm 80a to be changed incrementally. The ratchet component 102 and the tooth component 102 may also maintain a selected tilt forming a tilt lock component 105. In other embodiments, a tilt selection component may be separate from a tilt lock component, as the invention is not limited in this respect. A tilt lock component may maintain a force on one or both endplate surfaces as the first endplate preparation member 30 or both the first and the second endplate preparation members 30, 60 execute a sweeping motion.

Some embodiments of the invention may include one or more biasing components to bias the proximal first arm portion 50a and the proximal second arm portion 80a toward separation, which corresponds to a low profile, decreased tilt instrument configuration. In some embodiments, biasing components 106 may include springs 107, 108, as depicted. Further details regarding a collapsed configuration, an expanded configuration are described below with respect to FIGS. 5A and 5B.

Figure 1E:
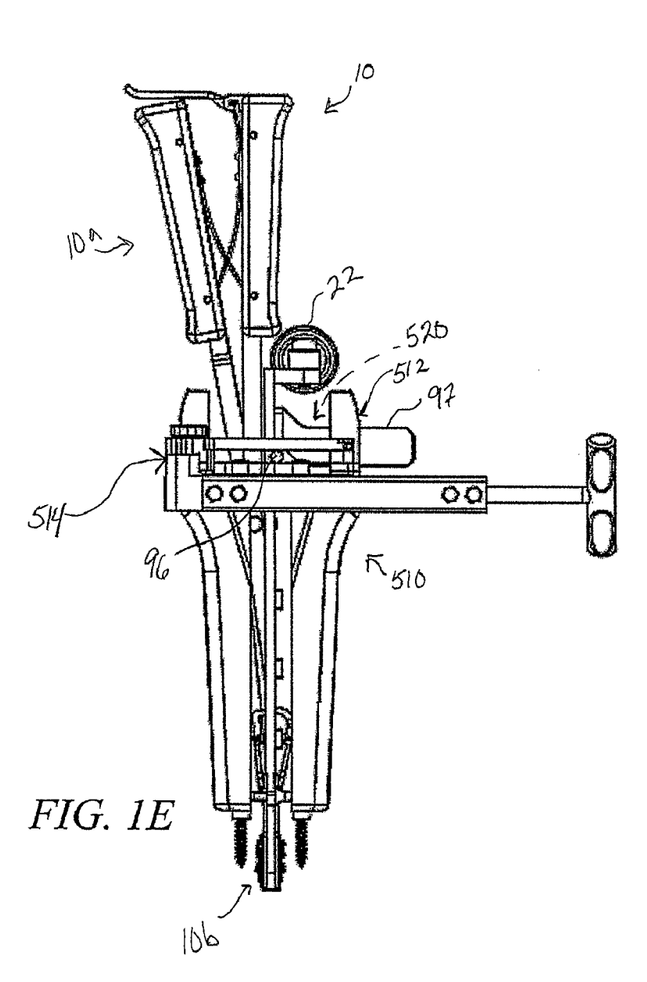
FIG. 1E is a side view of the instrument depicted in FIGS. 1A-1D engaging a distractor, in accordance with aspects of the invention.
Figure 1F:
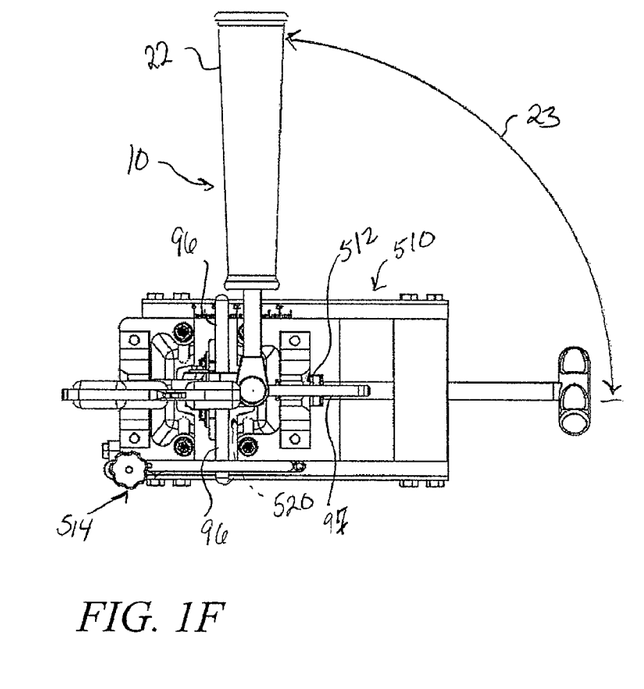
FIG. 1F is a top view of the instrument and the distractor depicted in FIG. 1E.

Some embodiments of the invention include additional elements that cooperate with coordinating elements on other instruments used during a surgical procedure. For example, a distal portion 10b of the instrument may be inserted into a disc space through a channel 520 formed by a distractor 510, as illustrated in FIGS. 1E and 1F. An alignment feature of the instrument 10, such as a keel projection 97, may cooperate with a coordinating alignment feature of the distractor 510, such as an alignment slot 512 configured to receive the keel projection 97, ensuring that the instrument 10 is properly aligned with the distractor 510 when it is inserted into the disc space. The instrument 10 may include at least one depth stop projection 96 that is engaged by a complementary depth stop feature 514 on a distractor to set a maximum insertion depth for insertion of the instrument 10 through the working channel 520 of the distractor 510. Further explanation of using exemplary endplate preparation instruments with distractors may be found in related co-pending U.S. patent application Ser. No. 12/115,043 entitled "DISTRACTOR," and filed on the same day as this application, and which is herein incorporated by reference in its entirety.

Exemplary embodiments may also include a frame handle 22 affixed to or integral with the frame 20. The frame handle 22 may be used for positioning and stabilizing the instrument during insertion and/or may engage complementary stabilization features on another surgical instrument such as a distractor or an external frame. In some embodiments, an orientation of the frame handle 22 is adjustable relative to the frame 20. For example, the frame handle 22 may pivot with respect to the frame 20 along arc 23.

Figure 2A:
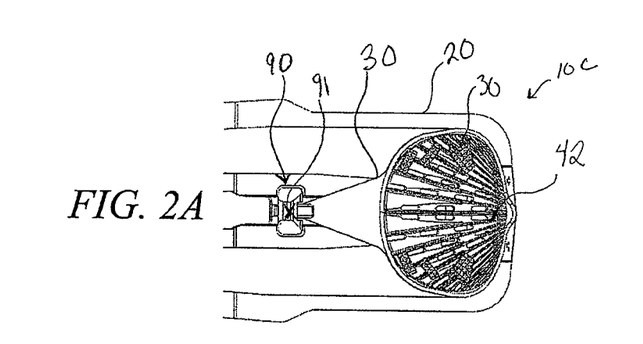
FIG. 2A is a side view of a distal portion of the instrument with a first endplate preparation member in a central sweep position, in accordance with an embodiment of the invention.
Figure 2B:
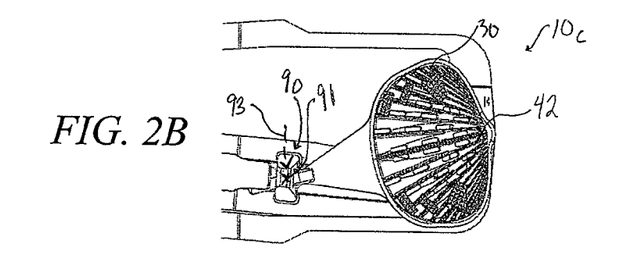
FIG. 2B is a side view of the distal portion of the instrument with the first endplate preparation member pivoted about a first axis with respect to the frame.
Figure 2C:
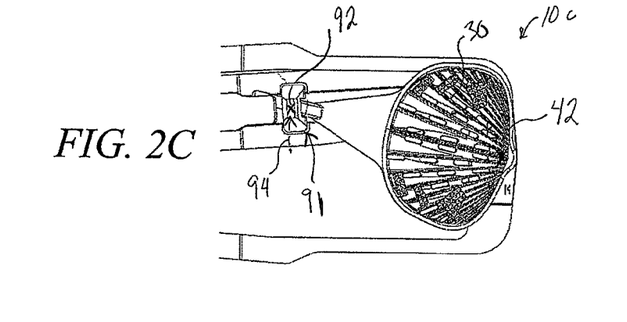
FIG. 2C is a side view of the distal portion of the instrument with the first endplate preparation member pivoted about the first axis with respect to the frame in an opposite direction illustrating a first member-arm coupling.

FIGS. 2A to 2D depict an enlarged distal portion 10b of the instrument with the first endplate preparation member 30 at different sweep positions, in accordance with an embodiment of the invention. FIG. 2A shows a side view of the enlarged distal portion 10b of the instrument with the first endplate preparation member 30 in a central sweep position with respect to the frame 20. The first endplate preparation member 30 is coupled with the first arm 50 by a first member-arm coupling 91, which is configured to allow the first endplate preparation member 30 to pivot with respect to the first arm 50 about a first member-arm axis 92 that is substantially parallel to the first sweep axis 42. FIGS. 2B and 2C, illustrate a sweeping motion of the first endplate preparation member 30 by showing side views of the distal portion of the instrument 10b with the first endplate preparation member 30 in one sweep position and in an opposite sweep position, respectively.

Figure 2D:
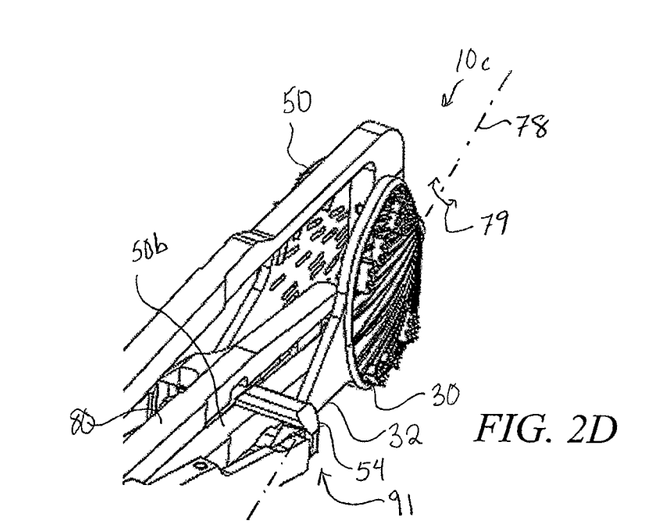
FIG. 2D is a perspective view of the distal portion of the instrument with the first endplate preparation member pivoted about the first axis further illustrating details of the first member-arm coupling, in accordance with aspects of the present invention.

FIG. 2D further illustrates a first preparation member-arm coupling 91 by showing an enlarged perspective view of a distal portion 10b of the instrument. In one embodiment, the first member-arm coupling 91 includes an extension 32 of the first endplate preparation member 30 that extends through an arch 54 of the first arm 50, as depicted. The interaction between the extension 32 of the endplate preparation member 30 and the arch 54 of the first arm acts as a pivotable coupling that allows the first preparation member 30 to pivot with respect to the first arm 50.

Figure 3:
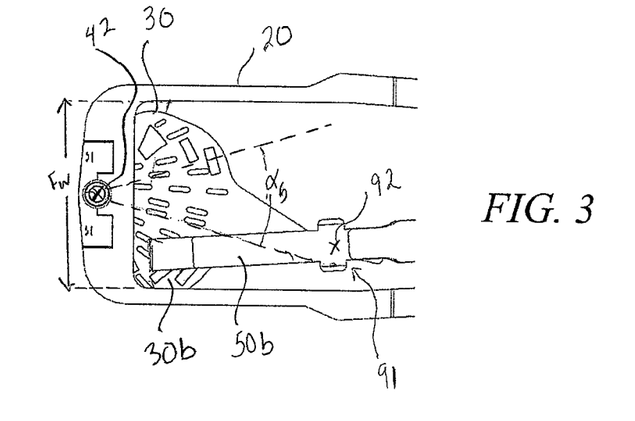
FIG. 3 is a side view of a distal portion of the instrument with the second endplate preparation member omitted to show a backside of the first endplate preparation member.

FIG. 3 provides a clear view of a backside of the first endplate preparation member 30 and the distal portion 50b of the first arm by omitting the second endplate preparation member 60 and the second arm 80. As shown in FIG. 3, the distal portion of the first arm 50b may extend behind the first endplate preparation member 30 past the first member-arm coupling 91. The first preparation member 30 and the first arm 50 also contact each other where the first arm 50 presses against the backside of the first preparation member 30. This contact allows the first arm to exert a force to tilt the first preparation member. Tilt of the first preparation member is described below in further detail with respect to FIGS. 5A and 5B.

An internal width $F_w$ of the frame 20 may limit a total range of sweep $\alpha_s$ of the first endplate preparation member 30 due to a portion of the frame 20 physically blocking a distal portion of the first arm 50b. As depicted, the first endplate preparation member is able to sweep though about ±13 degrees or a total sweep range of about 26 degrees. In some embodiments, a sweep range may be smaller, for example about ±1 degree or about 2 degrees total. In other embodiments, a sweep range may larger, for example about ±90 degrees or about 180 degrees total. However, other sweep ranges may be employed, as will be apparent to one of skill in the art.

In some embodiments, the first preparation member-frame coupling 41 and the first member-arm coupling 91 may be configured to allow the preparation member to rotate about a first "twist" axis 78 within a total "twist" range of less than about 180 degrees as indicated by arrow 79. The "twist" rotation may allow the first endplate preparation member 30 to adapt or conform to a rotational misalignment between the frame 20 and the disc space.

Some embodiments of the invention provide a first endplate preparation member 30 that is configured to be detached from an instrument. For example, in some embodiments, the first endplate preparation member 30 may be detachably connected with the frame 20. FIGS. 4A-4E show different views of the first endplate preparation member 30, in accordance with some embodiment of the invention. Although attributes and aspects of exemplary preparation members will be discussed with reference to the first endplate preparation member 30, any attributes and properties described with respect to the first endplate preparation member 30 may be incorporated into the second endplate preparation member 50 or an additional preparation member, as the invention is not limited in this respect.

The first endplate preparation member 30 may have a proximal portion 30p, a distal portion 30d, a front side 30f with a first preparation surface 31, a back side 30b and an edge 30e connecting the front side 30f and the back side 30b. A proximal portion 30p of the first endplate preparation member may include a pivot projection 32 that is configured to engage a feature of the first arm 50, such as the coupling arch 54, to form a portion of the first member-arm coupling 91 (see also FIG. 2D). The pivoting projection 32 may extend from the front side 30f and/or the edge 30e of the proximal portion 30p of the first endplate preparation member 30, in accordance with an embodiment of the invention. The pivoting projection 32 may be rounded facilitating more stable contact between the first endplate preparation member 30 and the coupling arch 54 as the first endplate preparation member 30 sweeps with respect to the frame 20, and as the first endplate preparation member 30 tilts with respect to both the frame 20 and the first arm 50 (see also FIG. 2D). A rounded surface of the pivoting projection 32 may allow the first endplate preparation member 30 to rotate about the first twist axis 78 (see also FIG. 2D).

The first endplate preparation member 30 includes one or more endplate preparation elements extending from the first preparation surface 31. The one or more endplate preparation elements may be configured to form one or more recesses or troughs, enlarge one or more recesses or troughs, shape one or more recesses or troughs, smooth one or more recesses or troughs and/or roughen one or more recesses and troughs in a vertebral endplate surface. The endplate preparation elements may include one or more primary cutting projections 33a, 33b, 33c that are configured to cut recesses or troughs into a vertebral surface. The recesses or troughs formed by the primary cutting projections 33a, 33b, and 33c may be primary fixation recesses configured to receive primary fixation features of an implant.

Figures 4A, 4B, 4C, 4D, 4E:
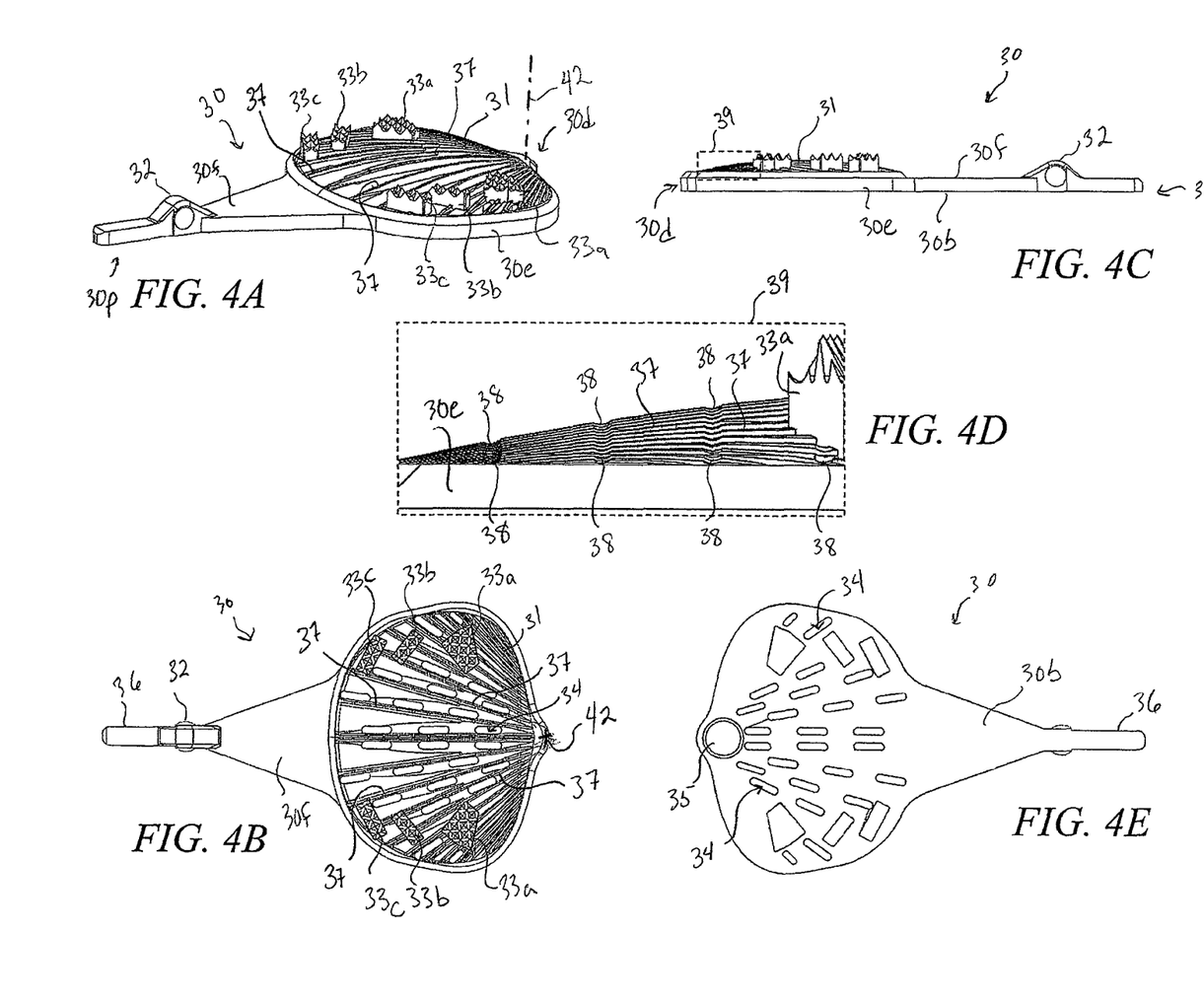
FIG. 4A is a perspective view of an illustrative preparation member, in accordance with an embodiment of the invention.
FIG. 4B is a view showing a front side of the illustrative preparation member depicted in FIG. 4A.
FIG. 4C is a view showing an edge of the illustrative preparation member depicted in FIG. 4A.
FIG. 4D is an expanded detail of FIG. 4C.
FIG. 4E is a view showing a back side of the illustrative preparation member depicted in FIG. 4A.

In some embodiments, the endplate preparation elements include dome-cutting projections 37 extending from the first preparation surface 31 configured to form, enlarge, shape and/or smooth a recess with a substantially domed shape, as shown in FIGS. 4A to 4D. In some embodiments, the dome-cutting projections 37 may be configured to enlarge, shape and/or smooth a pre-existing recess in a vertebral endplate. In some embodiments, at least some of the dome cutting projections 37 are elongated substantially radially outward from a first sweep axis 42 along the first preparation surface 31 as shown in FIGS. 4A and 4B. In some embodiments, each cutting projection 37 has a substantially curved profile, as shown in FIGS. 4A and 4D. A substantially curved profile of a dome cutting projection 37 may profile irregularities 38 configured to reduce a size of bone chips created by the dome cutting projection 37 during the endplate preparation process, as shown by FIG. 4D.

Although an exemplary embodiment of the first preparation member 30 is depicted with both primary cutting projections 33a, 33b, and 33c and dome-cutting projections 37, embodiments of the first preparation member may include primary cutting primary cutting projections 33a, 33b, and 33c, but not dome-cutting projections 37, may include dome-cutting projections 37, but not primary cutting primary cutting projections 33a, 33b, or may include neither, as the invention is not limited in this respect. The first preparation member 30 may include other types of suitable endplate preparation elements, as will be appreciated by one of skill in the art.

In some embodiments, the first endplate preparation member 30 may include channels 34 connecting the front side 30f and the backside 30b of the first endplate preparation member 30 that facilitate removal of debris during the endplate preparation process. FIG. 4E shows a region 35 on the back side 30b of the first endplate preparation member 30 that is configured to cooperate with the first preparation member-frame coupling 41 (see also FIG. 1A). In some embodiments, a proximal portion 30p of the first endplate preparation member 30 includes an extension portion 36 proximal to the pivoting projection 32.

The first endplate preparation member 30 illustrated in FIGS. 4A to 4E may be described as a rasp. However, other embodiments of the invention may include endplate preparation members in the form of rasps with other configurations, various types of cutting members, various types of grinders, combinations of cutting members and grinders, etc., as the invention is not limited in this respect.

Figure 5A:
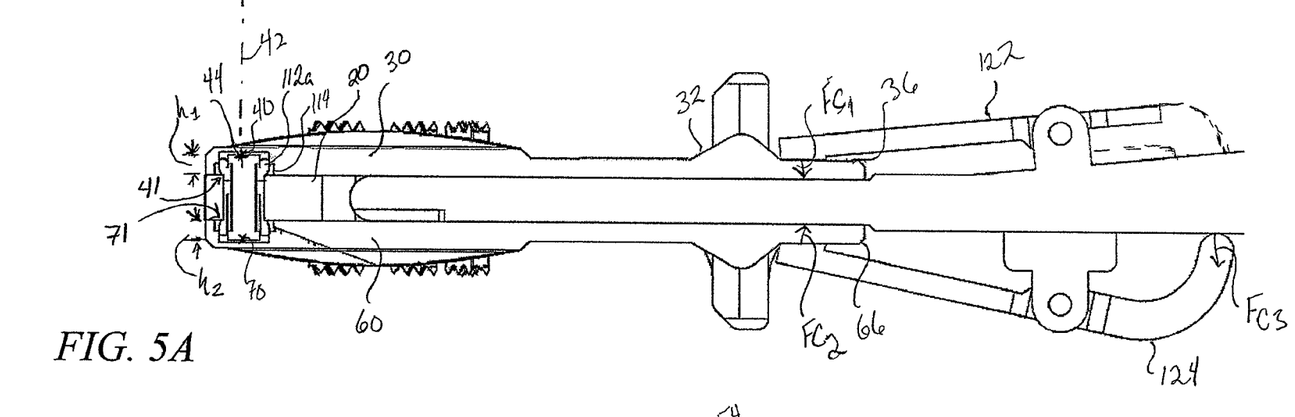
FIG. 5A is a top cross-sectional view of the distal portion of the instrument in a collapsed configuration, in accordance with aspects of the invention.
Figure 5B:
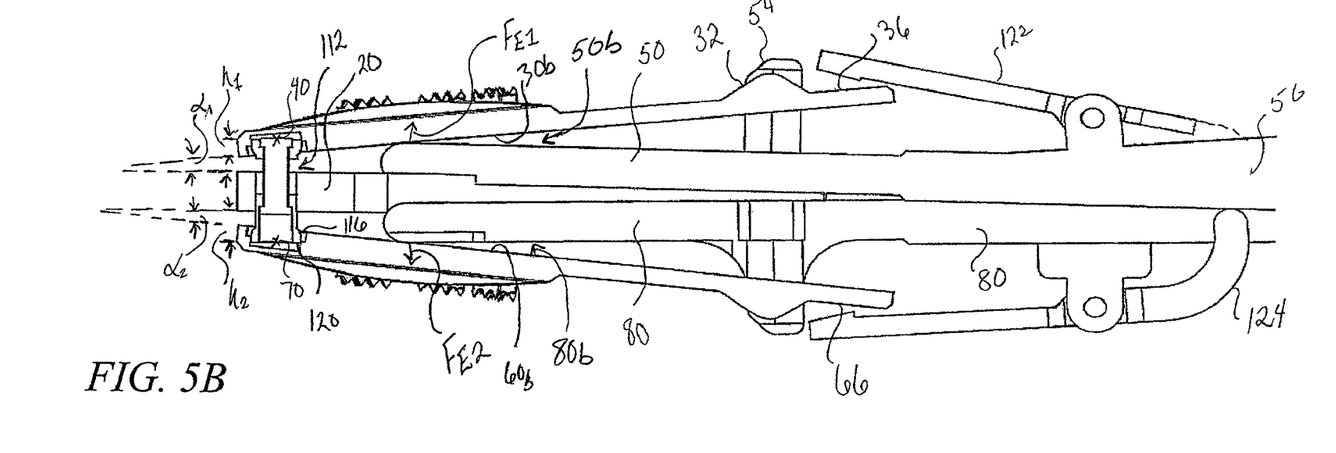
FIG. 5B is top a cross-sectional view of the distal portion of the instrument in an expanded configuration, in accordance with aspects of the invention.

FIGS. 5A and 5B depict cross-sectional views of a distal portion of instrument 10 illustrating a tilt α and a height h of the first endplate preparation member 30 and the second endplate preparation member 60 with respect to the frame 20, in accordance with aspects of the invention. FIG. 5A depicts a distal portion of the instrument 10b in a configuration for insertion or withdrawal. In the collapsed configuration, a tilt $\alpha_1$ of the first endplate preparation member 30 with respect to the frame 20 is relatively small and a separation $h_1$ between the first pivot point 40 and the frame 20 may be relatively small. For embodiments with a first endplate preparation member 30 and a second endplate preparation member 60, a tilt $\alpha_2$ of the second endplate preparation member 60 with respect to the frame 20 is relatively small in a collapsed configuration. A separation $h_2$ between the second pivot point 71 and the frame 20 may be relatively small in the collapsed configuration. For example, in FIG. 5A both the first endplate preparation member 30 and the second endplate preparation member 60 have zero tilt ($\alpha_1=0$ and $\alpha_2=0$).

FIG. 5B depicts the distal portion of the instrument 10b in an expanded configuration. The angle α1 between the first endplate preparation member 30 and the frame 20 is relatively larger in an expanded configuration. The separation h1 between the first pivot point 40 and the frame 20 may be relatively larger in an expanded configuration than in a collapsed configuration. For embodiments having a first endplate preparation member 30 and a second endplate preparation member 60, the tilt angle $\alpha_2$ between the second pivot point 70 and the frame 20 is larger in the expanded configuration. The separation $h_2$ between the second pivot point 70 and the frame 20 may be larger in an expanded configuration. The first preparation member-frame coupling 41 may be configured to allow the first endplate preparation member 30 to controllably change a tilt angle α with respect to the frame 20 and to change a height h with respect to the frame 20.

In some embodiments with both the first endplate preparation member 30 and the second endplate preparation member 60, the first preparation member-frame coupling 41 includes a first end 112a of a double-ended extendable pivot pin 112 and a first spherical retaining ring 114 attached to the first endplate preparation member 30. The second preparation member-frame coupling 71 may include a second end 112b of the double-ended extendable pivot pin 12 and a second spherical retaining ring 116 attached to the second endplate preparation member 60.

In some embodiments, a portion of the pivot pin 112 may be attached to the frame 20, as depicted. In some embodiments, the pivot pin 112 may connect the first endplate preparation member 30 and the second endplate preparation member 60, as depicted. In some embodiments, the pivot pin 112 may connect the first endplate preparation member 30 and the second endplate preparation member 50 and be slidably coupled with the frame 20, as the invention is not limited in this respect.

As described above with respect to FIGS. 1C and 1D, moving the proximal first arm portion 50a and the proximal second arm portion 80b toward each other, which causes the distal portion of the first arm 50b and a distal portion of the second arm 80b to move further apart, changes a configuration of the instrument 10 from collapsed to expanded. As illustrated by FIG. 5B, the proximal portion of the instrument 10b is expanded by the distal first arm portion 50b exerting a force $F_{E1}$ on the back side 30b of the first endplate preparation member and the distal second arm portion 80b exerting a force $F_{E2}$ on a back side 60b of the second endplate preparation member 60. The force $F_{E1}$ exerted by the first arm 50 pivots the first endplate preparation member 30 about the first pivot point 40 away from the frame 20. The first coupling arch 54, through which the first endplate preparation member 30 extends, sets a maximum tilt angle when the first pivot projection 32 engages the first coupling arch 54. As depicted, the tilt range as set by the maximum tilt angle is about 6 degrees for each of the first endplate preparation member 30 and the second endplate preparation member 60 for a total combined tilt range of about 12 degrees. In other embodiments, the tilt range may be smaller, for example, about 1 degree for each endplate preparation member for a total combined tilt range of about 2 degrees. However, other tilt ranges may be employed as will be apparent to one of skill in the art.

The force $F_{E1}$ exerted by the first arm 50 may also displace the first pivot point along the first sweep axis 42, displacing the first endplate preparation member 30 away from the frame 20. As depicted, the first pivot point 40 may be displaced when the extendable pivot pin 112 extends due to the force $F_{E1}$.

Similarly, force $F_{E2}$ exerted by the second arm 80 may pivot the second endplate preparation member 60 about the second pivot point 70 away from the frame 20. The second pivot point 70 may be displaced along the second sweep axis 72, when the extendable pivot pin 112 extends.

Conversely, spreading the first handle 52 and the second handle 82 apart, which causes the distal portion of the first arm 50b and the distal portion of the second arm 80b to move closer together, changes a configuration of the instrument 10 from extended to collapsed (see also FIGS. 1C and 1D). In some embodiments, a first reduction actuator 122 and/or a second reduction actuator 124 may be used to ensure that the first endplate preparation member 30 and/or the second endplate preparation member 60 remain in a collapsed configuration during insertion and withdrawal of the instrument 10, as depicted in FIG. 5A. Part of the first reduction actuator 122 is indicated by a dotted line because it lies in a plane that is not visible in the cross-sectional views of FIGS. 5A and 5B. The first reduction actuator 122, which is pivotably attached to the distal first arm portion 50b, exerts a force $F_{C1}$ on the extension portion 36 of the first endplate preparation member 30 to hold it against the distal portion of the first arm 50b. The second reduction actuator 124, which is pivotably attached to the distal second arm portion 80b, exerts a force $F_{C2}$ on an extension portion 66 of the second endplate preparation member 60 to hold it against the distal portion of the second arm 80b. Force $F_{C2}$ exerted by the second reduction actuator 124 on the second endplate preparation member 60 is due to a force $F_{C3}$ exerted by the first arm 50 on the second reduction actuator 124, as shown in FIG. 5A. Similarly, force $F_{C1}$ exerted by the first reduction actuator 122 on the first endplate preparation member 30 is due to a force (not depicted) exerted by the second arm 70 on the first reduction actuator 122.

The first reduction actuator 122 and the second reduction actuator 124 may allow a surgeon to ensure that the instrument is in a collapsed configuration. If the first endplate preparation member 30 and the second endplate preparation member 60 are not in a collapsed configuration, the first reduction actuator 122 and the second reduction actuator 124 prevent the first handle 32 and the second handle 62 from moving further apart.

Figure 6A:
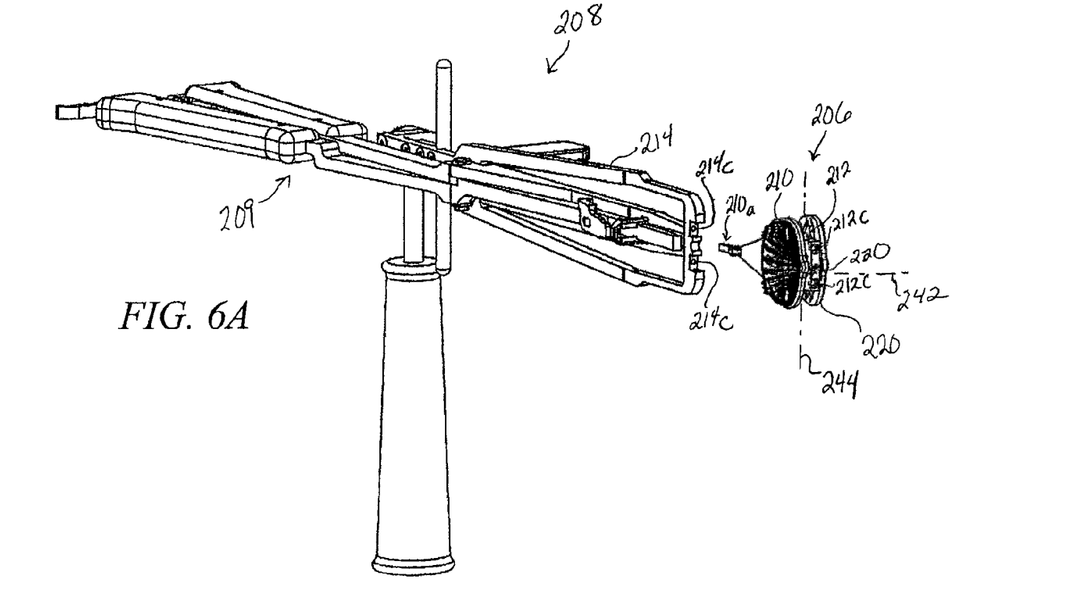
FIG. 6A is front perspective of an endplate preparation instrument having a removable preparation member unit, in accordance with another illustrative embodiment of the present invention.

Some embodiments of the invention may include a preparation member unit 206, as shown in FIG. 6A. Other embodiments of the invention include an instrument body 208. The preparation member unit 206 and the instrument body 208 are configured to couple to each other forming an endplate preparation instrument 208. The preparation member unit 206 may include a first endplate preparation member 210, a mounting member 212 configured to mount to a frame portion of the instrument body 208, and a first pivotable preparation member-mounting coupling 220 that couples the mounting member 212 and the first endplate preparation member 210. The first pivotable preparation member-mounting coupling 220 may be in the form of a pivot pin that extends through the mounting member 212 or a different type of coupling that is supported by the mounting member 212, as the invention is not limited in this respect.

In some embodiments, the preparation member unit 206 may also include a second endplate preparation member 215 that is coupled to the mounting member 212 by a second pivotable preparation member-mounting coupling 220. The first pivotable preparation member-mounting coupling 220 and the second pivotable preparation member-mounting coupling may be opposite ends of an extendable pivot pin disposed in the mounting member 212, or may be separate coupling elements each supported by the mounting member 212, as the invention is not limited in this respect.

In some embodiments, the mounting member 214 of the preparation member unit 206 may have channels 212c, and the frame portion 214 of the instrument body 208 may have threaded channels 214c allowing the mounting member 212 to be attached to the frame portion 214 using threaded screws. The first pivotable coupling 220 connects the mounting member 214 and the first endplate preparation member 210 allowing the first endplate preparation member 210 to pivot relative to the mounting member 220 about a first sweep axis 242 and about a first tilt axis 244 substantially perpendicular to the first sweep axis 242.

The preparation member unit 206 is detachable from the instrument body 208 and may be replaced with a different preparation member unit 206. Multiple different preparation member units 206 may be compatible with the same instrument body 208 allowing a surgeon to select from different sizes of endplate preparation members 210, endplate preparation members 210 with different preparation surface configurations, endplate preparation members 210 formed of materials with different material properties, etc.

The instrument body 208 includes a frame 214 configured to couple with the mounting member 220 of the preparation member unit 210, and an actuator 209 coupled with the frame 208 and configured to cooperate with the first endplate preparation member 210 of the preparation member unit 206. The actuator 209 is configured to controllably exert a force to pivot the first endplate preparation member 210 about a first sweep axis 242, and configured to controllably exert a force to pivot the first endplate preparation member 210 about a first tilt axis 244 that is substantially perpendicular to, and intersects, the first sweep axis 242. The actuator 209 may include a first arm and a second arm, as shown and described with respect to FIGS. 1A-2D above, may include a first arm and a tilt arm as described below with respect to FIGS. 7A-7D, or any other suitable configuration known in the art, as the invention is not limited in this regard.

Figure 6B:
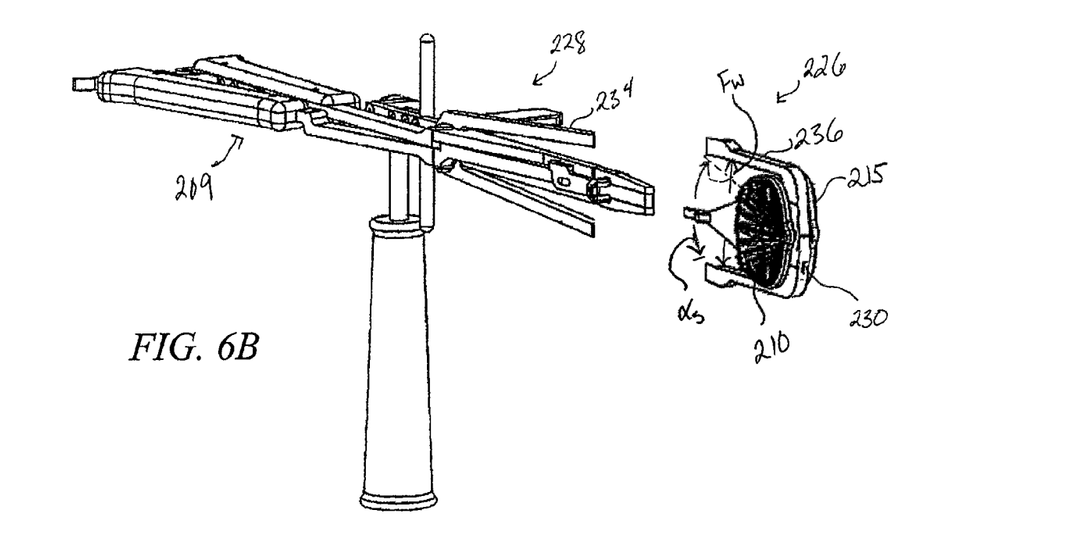
FIG. 6B is a front perspective view of an endplate preparation instrument having a removable preparation member unit that includes a distal frame portion, in accordance Is with another illustrative embodiment of the present invention.

Another embodiment of the invention including a preparation member unit 226 is depicted in FIG. 6B. The preparation member unit 226 is configured to mount to a frame portion 234 of an instrument body 228 forming an instrument. A frame of the total instrument includes a frame portion 234 of the instrument body 228 and a distal frame portion 236 of the preparation member unit 226. A mounting member 230 of the preparation member unit 226 may include the distal frame portion 236 of the preparation member unit. In some embodiments, the distal portion of the frame 236 may be configured to attach to the frame portion 234 of the instrument body 228 using screws, with a quick release mounting, or using any other method known in the art, as the invention is not limited in this regard. Known quick release mountings include, but are not limited to: various types of snap fit mountings, and various types of cam release mountings.

As explained above with respect to FIG. 3, an inner frame width $F_w$ may define a total maximum sweep angle $\alpha_s$ of a first endplate preparation member 210. Different preparation member units 226 may be provided with different internal frame widths $F_w$ allowing a surgeon to select a desired total maximum sweep angle $\alpha_s$ as well as a desired size and configuration of first endplate preparation member 210.

Although embodiments of an endplate preparation instrument depicted in the preceding figures showed two identical endplate preparation members, instruments with two differently sized endplate preparation members, instruments with two differently configured endplate preparation members, instruments with more than two endplate preparation members and instruments with one endplate preparation member also fall within the scope of the invention.

Figures 7A, 7B:
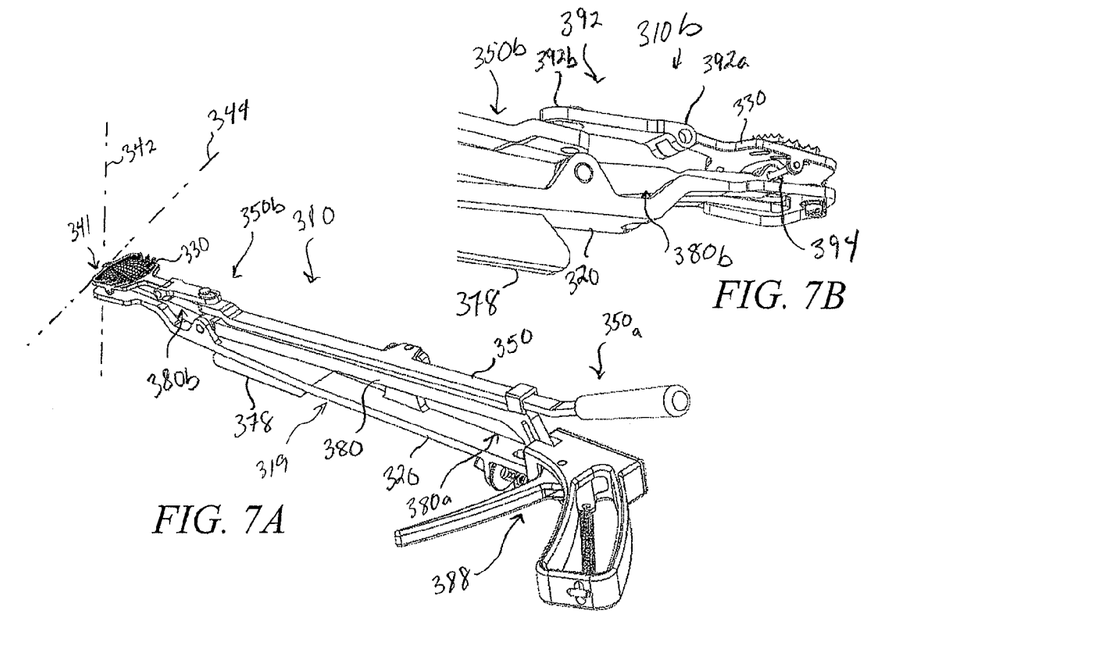
FIG. 7A is a perspective view of a vertebral endplate preparation instrument having one endplate preparation member and a trigger tilt mechanism in a collapsed configuration, in accordance with another embodiment of the invention.
FIG. 7B is an enlarged perspective view of a distal portion of the endplate preparation instrument preparation instrument depicted in FIG. 7A in a collapsed configuration.

For example, FIGS. 7A to 7D depict an endplate preparation instrument 310 having only one endplate preparation member 330, in accordance with another embodiment of the invention. Endplate preparation instrument 310 includes the endplate preparation member 330, a body 319 with a frame 320, a first (sweep) arm 350, and a tilt arm 380. FIG. 7A shows a perspective view of the instrument 310 in a collapsed configuration with the endplate preparation member 330 in a central sweep position. A pivotable preparation member-frame coupling 341 allows the endplate preparation member 330 to pivot about a sweep axis 342 and to pivot about a tilt axis 344 that is substantially perpendicular to the sweep axis 342. The first (sweep) arm 350 is used to control sweep of the endplate preparation member 330 and the tilt arm 380 is used to control tilt of the endplate preparation member 330.

Figures 7C, 7D:
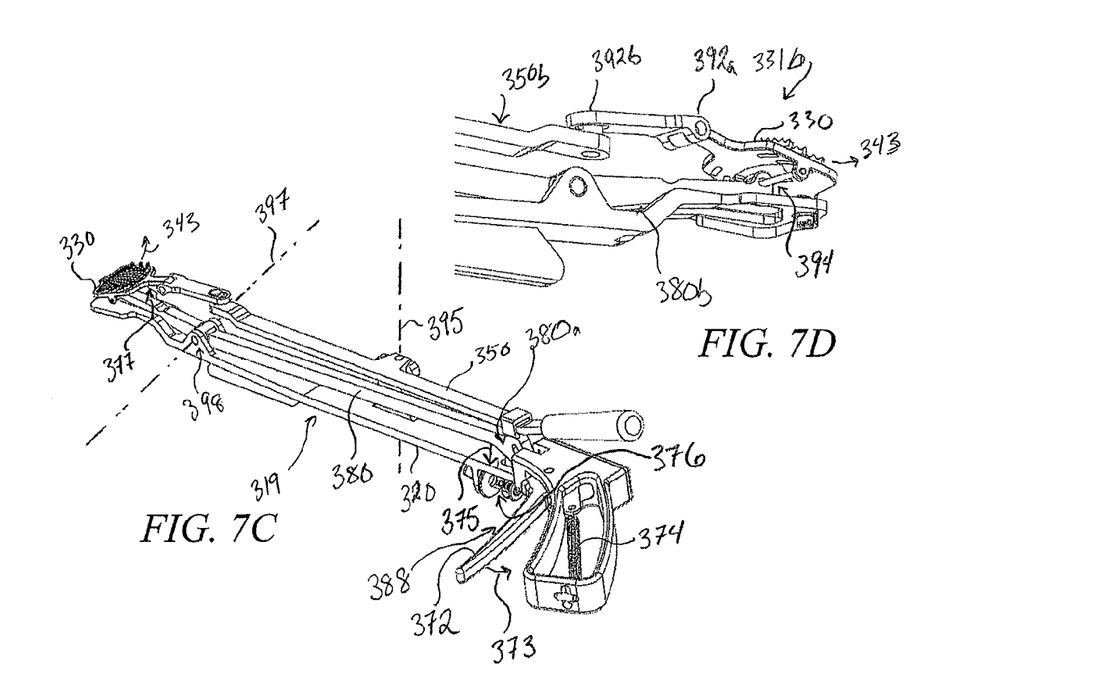
FIG. 7C is a perspective view of the vertebral endplate preparation instrument depicted in FIG. 7A in an expanded configuration.
FIG. 7D is an enlarged perspective view of the distal portion of the endplate preparation instrument depicted in FIG. 7A in an expanded configuration with the preparation member pivoted about the sweep axis.

FIG. 7B shows an enlarged perspective view of a distal portion 310b of the instrument. In this embodiment, a member-sweep-arm coupling 392 couples the endplate preparation member 330 and the sweep arm 350. The member-sweep-arm coupling 392 may include a rotatable coupling 392a and a sliding-pivotable coupling 392b, as shown in FIGS. 7B and 7D. A separate member-tilt-arm coupling 394 may slidably couple the endplate preparation member 330 and the tilt arm 380, as shown in FIGS. 7B and 7D.

In some embodiments, the first arm 350 is rotatably coupled with frame 320 allowing the first arm 350 to rotate with respect to the frame 320 about an arm-sweep axis 395 that is parallel to the sweep axis 342. In the depicted embodiment, the tilt arm 380 is rotatably coupled with frame 20 by the tilt-arm-frame coupling 398 allowing the tilt arm 380 to rotate about an arm-tilt axis 397. However, the tilt-arm-frame coupling 398 does not allow the tilt arm 380 to rotate about the arm-sweep axis 395. As shown in FIGS. 7C and 7D, although the endplate preparation member 330 has moved along arc 343 and the sweep arm 350 has rotated about axis 395 to change sweep position, the tilt arm 380 has not rotated about axis 395. The tilt arm 380 maintains contact with the endplate preparation member 330 during sweeps through the slidable member-tilt-arm coupling 394.

Endplate preparation instrument 310 may have a trigger-type tilt control 388T includes the tilt arm 380, and a trigger 372 coupled with a proximal portion 380a of the tilt arm 380. When the trigger 372 is depressed (arrow 373), the proximal portion 380a of the tilt arm rotates toward the frame 320 (arrow 375) causing the distal portion 30d of the tilt arm to rotate away from the frame 20 (arrow 377), thereby increasing a tilt of the endplate preparation member 330, as shown in FIG. 7C. The trigger-type tilt control 388 may include a biasing element (e.g. spring 374) to bias the instrument 310 toward a collapsed configuration. In some embodiments, the trigger-type tilt control 388 may include a maximum tilt selection component and tilt lock component 376. The instrument 310 may also include one or more alignment features 378 to aid in aligning the instrument for insertion into a disc space, as shown in FIGS. 7A and 7B.

Figure 8:
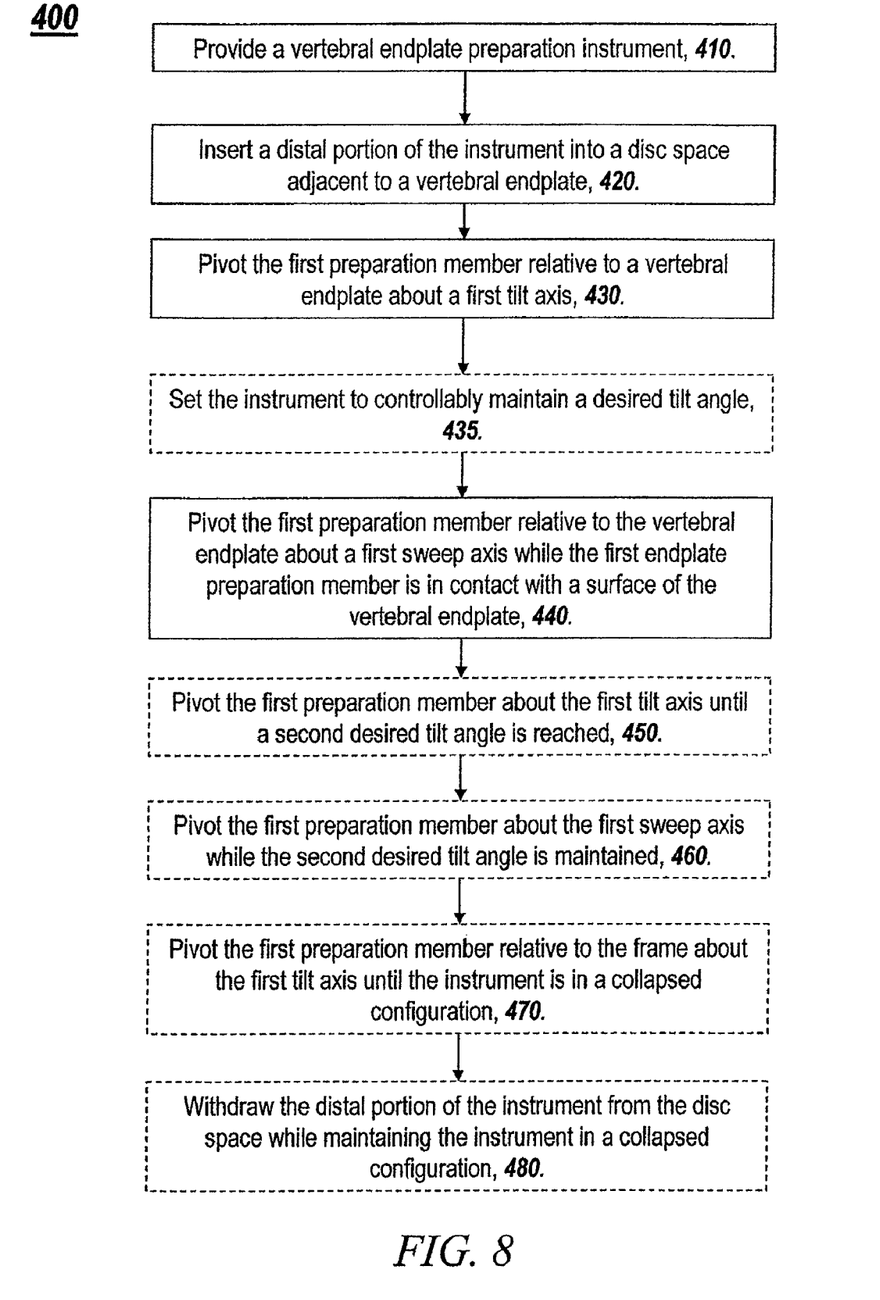
FIG. 8 is a flow chart illustrating a method of using an endplate preparation instrument to prepare vertebral endplates, in accordance with another embodiment of the invention.

Other exemplary embodiments include a method 400 of preparing a vertebral endplate, as illustrated in the flow chart of FIG. 8. Solely for illustrative purposes, method 400 will be described with respect to the endplate preparation instrument 10 depicted in FIGS. 1A-1D. One of skill in the art will recognize that method 400 may be performed with other exemplary instruments, as the invention is not limited in this respect.

Initially, a vertebral endplate preparation instrument 10 having a first endplate preparation member 30 at a distal portion 10b of the instrument is provided (step 410). The instrument includes a frame 20 and a first endplate preparation member 30 disposed at a distal portion of the instrument 20b. The instrument also includes a first pivot point 40 where a first sweep axis 42 intersects a first tilt axis 44 that is substantially perpendicular to the first sweep axis 42 at pivot point 40.

The distal portion 10b of the instrument is inserted into a disc space adjacent to a vertebral endplate (step 420). In some embodiments, the instrument 10 is in a collapsed configuration when the distal portion 10b of the instrument is inserted into the disc space (see also FIG. 5A). The first endplate preparation member 30 is pivoted relative to the vertebral endplate about a first tilt axis 44 (step 430), (see also FIG. 5B). The first endplate preparation member 30 may be pivoted until a first desired tilt angle $\alpha_1$ is reached. In some embodiments, the method also includes setting the instrument 10 to controllably maintain the tilt angle $\alpha_1$ (step 435). The instrument may be set using a ratchet mechanism, a tilt lock or any other suitable element or technique known to one of skill in the art.

The first endplate preparation member 30 is pivoted relative to the vertebral endplate about a first sweep axis 42 that is substantially perpendicular to the first tilt axis 44 while the endplate preparation member 30 is in contact with the first vertebral endplate surface (step 440). In some embodiments, the first desired tilt angle $\alpha_1$ is maintained while the first endplate preparation member 30 is pivoted about the first sweep axis 42. In some embodiments, the instrument includes a frame 20 and the frame 20 is stationary with respect to the vertebral endplate while the first endplate preparation member 30 is pivoted with respect to the vertebral endplate. In some embodiments, a user of the instrument 10 has manual feedback regarding forces applied to the vertebral endplate during the sweeping motion by feeling a resistance to the sweeping motion.

In some embodiments, the first endplate preparation member 30 may be pivoted about the first tilt axis 42 until the first endplate preparation member 30 reaches a second desired tilt angle, which is larger than the first desired tilt angle (step 450). The first endplate preparation member 30 may then pivot relative to the frame 20 about the first sweep axis 42 while maintaining the second desired tilt angle (step 460). Incrementally increasing the tilt angle and sweeping the first endplate preparation member at each new tilt angle can gradually increase a depth of a feature in an endplate reducing stress on the vertebra as compared to more aggressive techniques. In some embodiments, the frame 20 of the instrument 10 can remains stationary with respect to the vertebra as the first endplate preparation member 30 is pivoted about the first tilt axis 42 and as the first endplate preparation member is pivoted about the first sweep axis.

In some embodiments, the instrument 10 also includes a second endplate preparation member 60 disposed at the distal portion 10b of the instrument and a second pivot point 70. A second sweep axis 72 and a second tilt axis 74 that is substantially perpendicular to the second sweep axis 72, intersect at the second pivot point 70. The method may also include pivoting the second endplate preparation member 60 relative to the vertebral endplate about the second tilt axis 74 to change a tilt angle of the second endplate preparation member 60, and pivoting the second endplate preparation member 30 relative vertebral endplate about the second sweep axis 72 while maintaining the tilt angle. The second endplate preparation member 60 may be moved simultaneously with the first endplate preparation member 30, or may move independently. If the second endplate preparation member 60 does not move at a same time as the first endplate preparation member 30, the frame 20 of the instrument may remain in a same position for the sweeping motion of the first endplate preparation member 30 and the sweeping motion of the second endplate preparation member 60.

According to some embodiments of the invention, the first endplate preparation member 30 is pivoted relative to a frame 20 of the instrument about the first tilt axis 44 until the distal portion 10b of the instrument is in a collapsed configuration (step 470). The distal portion 10b of the instrument is then withdrawn from the disc space while maintaining the instrument 10 in a collapsed configuration (step 480). Inserting and removing the distal portion 10b of the instrument from the disc space with the instrument 10 in a collapsed configuration may reduce a risk that the first endplate preparation member 30 and/or the second endplate preparation member 60 damage one or both vertebral endplates during insertion or removal.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A surgical instrument for preparing a surface of a vertebra, the instrument comprising:
   an elongated body including a frame;
   a first pivot point, wherein a first sweep axis and a first tilt axis that is substantially perpendicular to the first sweep axis pass through the first pivot point; and
   a first endplate preparation member for preparing a surface of a vertebra that is supported by the body and that is controllably pivotable in an arc about the first tilt axis to change a tilt of the first endplate preparation member, and is controllably pivotable in an arc about the first sweep axis while maintaining a tilt of the first endplate preparation member.

2. The instrument of claim 1, wherein the first endplate preparation member is pivotable with respect to the frame about the first tilt axis and pivotable with respect to the frame about the first sweep axis.

3. The instrument of claim 1, wherein the first endplate preparation member is pivotably coupled to the frame.

4. The instrument of claim 1, further comprising:
   a second pivot point, wherein a second sweep axis and a second tilt axis that is substantially perpendicular to the second sweep axis intersect at the second pivot point; and
   a second endplate preparation member for preparing a surface of a vertebra that is controllably pivotable in an arc about the second tilt axis to change a tilt of the second endplate preparation member, and is controllably pivotable in an arc about the second sweep axis while maintaining a tilt of the second endplate preparation member.

5. The instrument of claim 4, wherein the second sweep axis has substantially a same position and a same orientation as the first sweep axis.

6. The instrument of claim 1, wherein the first endplate preparation member is controllably pivotable about the first tilt axis and about the first sweep axis simultaneously.

7. The instrument of claim 1, wherein the first pivot point is able to move along the first sweep axis changing a height of the first endplate preparation member with respect to the frame.

8. The instrument of claim 1, wherein an inner width of the frame at the distal portion of the instrument at least partially determines a total angular sweep range for the first endplate preparation member.

9. The instrument of claim 1, wherein a total sweep range is at least about 2 degrees.

10. The instrument of claim 1, wherein a tilt range for the first endplate preparation member is at least about 1 degree.

11. The instrument of claim 1, wherein the first endplate preparation member is configured to be detached from the instrument.

12. The instrument of claim 1, wherein the first endplate preparation member is detachably connected with the frame.

13. The instrument of claim 1, wherein a preparation member unit of the instrument is removable and replaceable, and wherein the preparation member unit comprises:
   the first endplate preparation member;
   a mounting element configured to engage a corresponding mounting portion disposed on the frame; and
   a first preparation member-frame coupling that pivotably couples the first endplate preparation member and the mounting element.

14. The instrument of claim 13, wherein the preparation member unit further comprises:
   a second endplate preparation member; and
   a second preparation member-frame coupling that pivotably couples the second endplate preparation member and the mounting element.

15. The surgical instrument of claim 1, further comprising a first arm that is controllably pivotable with respect to the frame and configured to cooperate with the first endplate preparation member for controllably pivoting the first endplate preparation member about the first sweep axis.

16. The surgical instrument of claim 1, further comprising an actuator that is coupled with the frame, that is configured to cooperate with the first endplate preparation member, configured to controllably pivot the first endplate preparation member about the first sweep axis, and configured to controllably pivot the first endplate preparation member about the first tilt axis.

17. The instrument of claim 1, wherein at least one of the first tilt axis and the first sweep axis extends through the first endplate preparation member.

18. The instrument of claim 17, wherein the first pivot point is positioned at a distal end of the frame.

19. An instrument for preparation of a surface of a vertebral endplate, the instrument comprising:
   a first endplate preparation member disposed at a distal portion of the instrument;
   means for pivoting the first endplate preparation member relative to the vertebral endplate about a first tilt axis; and
   means for pivoting the first endplate preparation member relative to the vertebral endplate about a first sweep axis that is substantially perpendicular to the first tilt axis while the first endplate preparation member is in contact with the vertebral endplate surface.

20. The instrument of claim 19, further comprising:
   means for setting the instrument to controllably maintain a tilt angle.

21. The instrument of claim 19, wherein the means for pivoting the first endplate preparation member about the first tilt axis allow a configuration of the instrument to be changed to a collapsed configuration.

22. The instrument of claim 19, wherein the means for pivoting the first endplate preparation member about the first sweep axis and the means for pivoting the first endplate preparation member about the first tilt axis allow the first endplate preparation member to be pivoted about the first sweep axis and pivoted about the first tilt axis simultaneously.

23. The instrument of claim 19, wherein at least one of the first tilt axis and the first sweep axis extends through the first endplate preparation member.

* * * * *